(12) United States Patent
Tyvoll et al.

(10) Patent No.: US 7,726,303 B2
(45) Date of Patent: Jun. 1, 2010

(54) CONTROLLED MEDICAMENT EJECTION

(75) Inventors: David Tyvoll, La Jolla, CA (US); Winthrop D. Childers, San Diego, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 1094 days.

(21) Appl. No.: 10/375,794

(22) Filed: Feb. 25, 2003

(65) Prior Publication Data

US 2004/0163641 A1  Aug. 26, 2004

(51) Int. Cl.
*A61M 15/00* (2006.01)
(52) U.S. Cl. .................................. 128/200.21
(58) Field of Classification Search ............ 128/200.21, 128/200.22, 204.15, 204.16, 204.17
See application file for complete search history.

(56) References Cited

U.S. PATENT DOCUMENTS

| 5,331,953 | A | 7/1994 | Andersson et al. |
| 5,363,842 | A | 11/1994 | Mishelevich et al. |
| 5,469,750 | A | 11/1995 | Lloyd et al. |
| 5,608,647 | A | 3/1997 | Rubsamen et al. |
| 5,692,492 | A | 12/1997 | Bruna et al. |
| 5,755,218 | A * | 5/1998 | Johansson et al. ...... 128/200.14 |
| 5,880,748 | A | 3/1999 | Childers et al. |
| 5,881,716 | A | 3/1999 | Wirch et al. |
| 5,894,841 | A | 4/1999 | Voges |
| 6,158,431 | A * | 12/2000 | Poole ..................... 128/203.12 |
| 6,196,218 | B1 * | 3/2001 | Voges .................... 128/200.14 |
| 6,196,219 | B1 * | 3/2001 | Hess et al. ............. 128/200.21 |
| 6,234,167 | B1 * | 5/2001 | Cox et al. .............. 128/200.14 |
| 6,540,154 | B1 * | 4/2003 | Ivri et al. ....................... 239/11 |
| 2001/0032647 | A1 * | 10/2001 | Schuster et al. ........ 128/204.17 |
| 2002/0079309 | A1 | 6/2002 | Cox et al. |
| 2002/0187248 | A1 | 12/2002 | Childers |
| 2004/0112380 | A1 * | 6/2004 | Djupesland ............ 128/203.12 |
| 2005/0099465 | A1 * | 5/2005 | Silverbrook .................. 347/60 |

FOREIGN PATENT DOCUMENTS

EP  1 306 219  5/2003

* cited by examiner

*Primary Examiner*—Todd E Manahan
*Assistant Examiner*—Eric Blatt

(57) ABSTRACT

Controlled ejection of a fluid-based solute medicament includes determining an indication of a characteristic of the medicament in at least one ejection chamber, and ejecting the medicament from the at least one ejection chamber based on the determined indication.

3 Claims, 4 Drawing Sheets

CONTROLLED MEDICAMENT EJECTION

BACKGROUND

Fluid-based medicament ejectors are used to dispense medicament as an aerosol. An example of such an ejector is the metered dose inhaler. Metered dose inhalers provide a much-needed drug-delivery method that allows patients to aspirate medication rather than swallow a pill, or drink or inject medication. In some cases, as with medications that directly target the patient's lungs, aspiration enables the medicine to reach the target area more quickly. In addition, aspiration is typically considered to be less painful than other drug-delivery methods.

As with other methods of taking medications, it is desired that the dosage levels be determinable and consistent. With solid or liquid medicaments, dosage level may be fairly accurately established. However, aerosol-based medicaments may be more difficult to administer accurately. For one reason, a mechanical device typically is relied upon to generate a dosage. It is also more difficult for a patient to receive a dosage effectively. For instance, with an inhaler, the patient must inhale an aerosol spray containing the medicament. The effectiveness of the dosage may depend, for example, on how well the patient inhales, and the orientation and position of the inhaler relative to the patient's mouth.

Effective delivery of aerosol medicaments also may depend on the consistent functioning of the inhaler. In particular, the inhaler should produce a desired quantity of medicament during a period of time that allows the aerosol medicament to be inhaled by the patient. The quantity of medicament is not the only issue with aerosols. It has been shown that the velocity and aerodynamic particle size of the droplet influence the location of aerosol deposition in the lung. Particles that are larger than approximately 6 microns tend to deposit in the mouth and trachea. Particles that are between approximately 2-6 microns tend to deposit in the bronchi and bronchioles. Particles that are between approximately 0.5-2 microns tend to deposit in the terminal bronchioles and alveoli. The deposition of particles below approximately 0.5 microns is minimal, these particles are more susceptible to being expelled upon exhalation. For many drugs, deposition in the lower airways is most desirable, and hence require aerodynamic particle sizes in the range of approximately 1-5 microns. Metered dose inhalers may produce a large range of droplet sizes within a single puff, including droplets both above and below the ideal range. Those droplets that are too small are not retained by the lungs, and are instead exhaled out of the body. Likewise, those droplets that are too large are not absorbed by the lungs, but instead deposit in the extrathoracic and upper airways. They are subsequently swallowed and absorbed in the gastrointestinal tract. As a result, in order to obtain dependable and consistent results with aerosol-based medicament ejectors, it is useful to maintain consistent quantity and quality of dosages.

SUMMARY

Controlled ejection of a fluid-based solute medicament includes determining an indication of a characteristic of the medicament in at least one ejection chamber, and ejecting the medicament from the at least one ejection chamber based on the determined indication.

DETAILED DESCRIPTION

Figure 1:
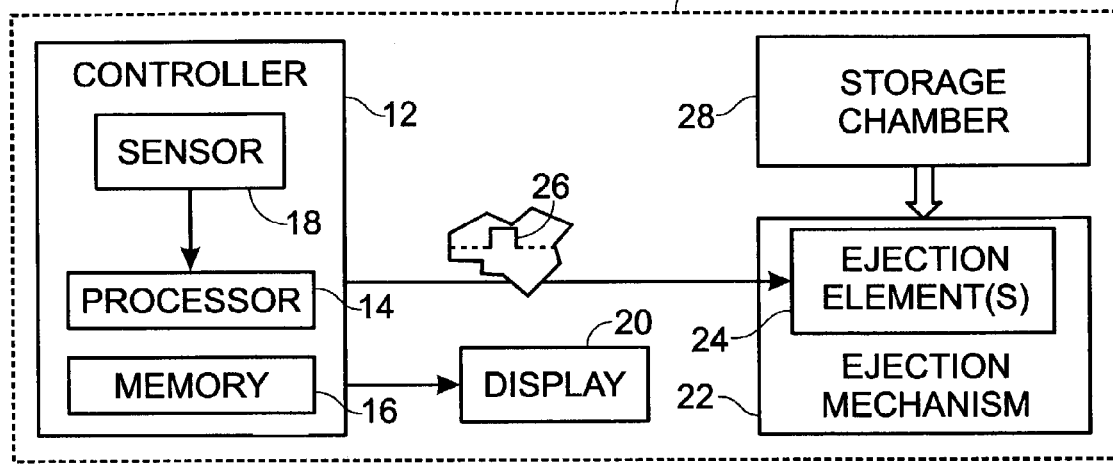
FIG. 1 is a block diagram of a medicament ejector according to an embodiment of the present invention.
Figure 2:
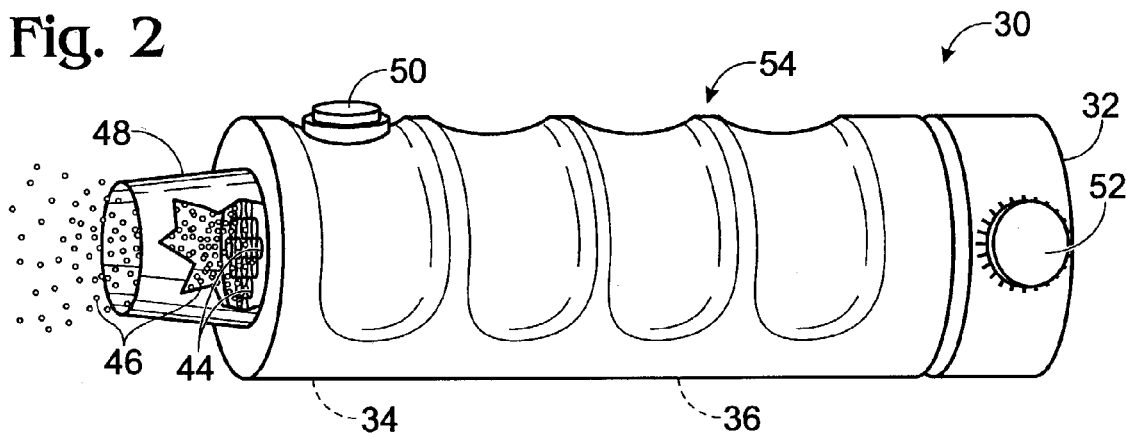
FIG. 2 is a side view of a metered dose inhaler according to another embodiment of the present invention.

An ejector configured to eject a fluid-based solute medicament is indicated generally at 10 in FIG. 1. Ejector 10 thus may be configured to eject an aerosol medicament, such as may be provided by a metered dose inhaler according to an embodiment of the present invention. The medicament may be entrained or otherwise mixed, such as in solution in a fluid, gas or liquid. Accordingly, the medicament may be referred to as a fluid-based solute medicament.

As shown, ejector 10 may include a controller 12 adapted to control ejector 10 electronically, mechanically, or both. Controller 12 thus may include a processor 14 and memory 16 configured to store preprogrammed operating parameters. Memory 16 may include volatile memory, nonvolatile memory, or both. It is to be appreciated that such operating parameters may be provided via direct user input, may occur via a personal computer or other device, or be in the form of firmware. The controller may provide a prescribed dosage or nominal dosage, and/or may be provided with dosage parameters such as a loading dosage and/or a dosing regimen set by a physician, pharmacist, or manufacturer of the prescribed medicament.

Various input mechanisms also may be provided, such as sensor 18, which may provide the processor with information regarding indications of characteristics of medicament to be ejected, such as the pressure or temperature of the medicament, as is discussed in further detail below. In the depicted embodiment, dosage information as well as audible or visible alarm conditions, and other desired information may be communicated to a display 20 for communication with a user. Accordingly, controller 12 may also be referred to as structure for determining an indication of a characteristic of medicament.

Figure 3:
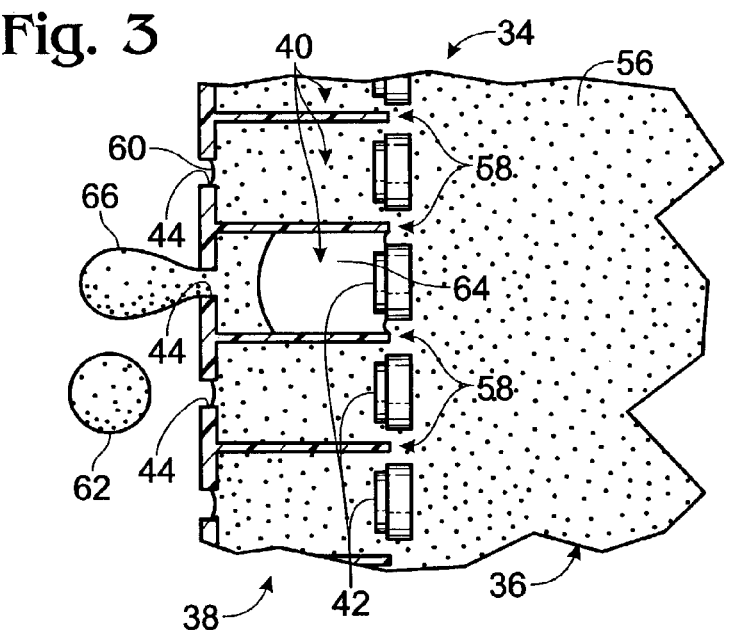
FIG. 3 is a somewhat simplified illustration of an ejection mechanism according to an embodiment of the present invention.

As indicated, controller 12 also may be in electronic communication with an ejection mechanism 22 so as to provide controlling direction to one or more ejection elements 24. Mechanism 22 may also be referred to as structure for ejecting medicament. Typically, such direction may be in the form of a transmission of an electronic signal 26 to one or more ejection elements 24 to effect activation of such element(s), and thus, to effect controlled ejection of droplets of medicament as an aerosol, such as is described with respect to FIG. 3. The ejection elements receive fluid-based medicament from a storage chamber 28, also referred to as structure for storing medicament. The character and frequency of such electronic signals may be determined by processor 14 based on the desired dosage, drop size, or other medicament dosage characteristic to be produced. The desired medicament dosage characteristic may be defined by user input, by pre-programmed parameters, or by adaptive controller programming as described herein.

Accordingly, processor 14 may direct transmission by controller 12 of a single pulse to one or more ejection elements so as to effect a single activation or firing of one or more ejection elements, and correspondingly, to produce a single set of aerosol droplets of medicament. Alternatively, the controller may transmit a series of rapid-succession pulses at a selected rate so as to successively activate one or more of the ejection elements, thereby producing a longer duration “puff” of medicament droplets than that previously mentioned. Other signals may prepare the medicament in the ejection chamber for ejection by varying a characteristic of the medicament to produce ejected medicament having desired characteristics, such as a particular dosage or drop size.

Another embodiment of the present invention is shown in a side and partial cut-away view in FIG. 2. A medicament ejector in the form of an inhaler 30 includes a body 32 having an ejection mechanism 34 in fluid communication with a medicament storage chamber 36. Mechanism 34 may also be referred to as structure for vaporizing inhalant. As will be appreciated upon reading further, ejection mechanism 34 may be configured to effect ejection of a selected dosage of medicament/inhalant from inhaler 30 in response to a signal sent by a controller (as described above with reference to FIG. 1). Suitable medicaments include those typically found in liquid, solid, powder, paste or other forms.

Turning now to FIG. 3, a somewhat simplified fragmentary illustration of one possible interior configuration of inhaler 30 is depicted, the illustration being confined generally to the vicinity of ejection mechanism 34. Focusing initially on ejection of the medicament, it is to be understood that ejection mechanism 34 may include a vaporization region 38 within one or more ejection chambers 40, each with an element 42 configured to eject vaporized droplets of medicament. As indicated, this region may define a plurality of orifices 44 that produce the vaporized, or atomized, droplets of medicament in inhalant stream 46 (FIG. 2).

Orifices 44 may feed into a mouthpiece 48, which may be placed in the patient’s mouth in order to facilitate administration of the medicament to the patient in what is referred to herein as a dosing event. As will be appreciated, however, mouthpiece 48 may take alternative forms, including forms that may be adapted to fit over a patient’s mouth and/or nose.

Inhaler 30 may further include one or more user inputs that facilitate communication between the user and the inhaler’s controller. This communication may include directives and/or information communicated from the user to the controller, and vice versa. For example, activation input 50 may be configured to communicate a directive from the user to the controller to initiate a dosing event. In the present invention, illustration input 50 takes the form of a depressible button, as shown in FIG. 2, but could take the form of a trigger, switch, touch-sensitive button, or the like. Activation input 50 is depicted on top of body 32, but it will be appreciated that such input may be positioned in virtually any other location convenient to the user. Activation input may also be through a device that senses the inhalation of a user.

FIG. 2 also shows a display 52 which may be, for example, an LCD display adapted to display information to the user, an LED or other light, an audible speaker, or a combination of such devices. It may also take the form of a mechanical counter, a mechanical gauge, or some other suitable device.

Display 52 may be adapted to provide the user alarm information, as well as with dosage information, such as the number of doses administered and/or the number of doses remaining in the inhaler. In some instances, however, display 52 may also be adapted to provide the user with information such as the nature of an alarm condition, such as there being insufficient medicament for an additional dosage, a medicament characteristic prevents operation of the inhaler, or the inhaler is positioned at an incorrect orientation. Moreover, the display may enable two-way communication between the user and the inhaler, for example, through use of a touch screen or other device.

As further shown in FIG. 2, body 32 may be shaped to provide gripping regions 54 so as to accommodate the hand and/or fingers of the user. As will be appreciated, alternative configurations of inhaler 30 are contemplated, including an L-shape, wherein the medicament storage chamber is located in an upright fashion, generally perpendicular to the mouthpiece.

As previously stated, ejection mechanism 34 may be in fluid communication with medicament reservoir or storage chamber 36, which may serve to store medicament 56 prior to dosing. In the embodiment shown in FIG. 3, each of ejection chambers 40 are in fluid communication with medicament storage chamber 36, for example, via fluid channels 58. Channels 58 may also be referred to as structure for transferring inhalant to the vaporizing structure. Passage of the medicament from the medicament storage chamber 36 to ejection chambers 40 may be either active or passive. For example, ejection of medicament within an ejection chamber may itself produce a vacuum sufficient to draw more medicament into the ejection chamber. Alternatively, gravity, or more active forms of transportation, including pumps or other mechanical or electronic structure may be employed. These ejection chambers are also referred to as vaporization chambers.

The ejection chambers are each adapted to receive and contain a charge of fluid medicament, as indicated for example, in uppermost complete ejection chamber in FIG. 3. This may be accomplished, in part, due to the geometry of the ejection chamber, which may lead to formation of a meniscus 60 in the chamber’s ejection orifice, due in part to a backpressure from storage chamber 36. Backpressure, it will be appreciated, also may be referred to as gauge pressure—which is defined relative the outside atmospheric pressure. This backpressure may be in the range of −1 to −10 inches of water, depending on the characteristics of the drop generator geometry and the fluid properties (such as surface tension). The ejection chambers, it will be appreciated, open to the inhaler mouthpiece via nozzles or ejection orifices 44, but typically do not freely pass medicament through the orifices due to menisci such as that shown at 60. Without sufficient backpressure, the medicament may seep out of the orifices.

Each ejection chamber may include at least one ejection element 42 configured to selectively controllably eject medicament from within the corresponding ejection chamber as a vaporized medicament droplet 62. In the present embodiment, the ejection element (also referred to as a vaporization element) takes the form of a heating element opposite the chamber’s ejection orifice. In response to an ejection signal (e.g., a predetermined voltage applied across a heating element), the heating element may be activated, heating medicament in the vicinity of the heating element. Such heated medicament, in turn, expands toward the ejection orifice, overcoming opposing forces of the meniscus and backpressure, and forcing more distal medicament out of the ejection orifice in a predicable-size vapor droplet. Such ejection is demonstrated in FIG. 3.

In the second ejection chamber of FIG. 3, the ejection element will be seen to superheat medicament in its vicinity to produce a bubble 64 which is shown expanding toward the ejection orifice. The advancing bubble, in turn, will be seen to urge medicament, which was previously within the ejection chamber, out through the ejection orifice so as to form a vapor droplet 66. The size and trajectory of this ejected vapor droplet may be predicted to within a range based on the size and shape of ejection chamber 40, as well as the power dissipated in the chamber and the pressure and temperature of the medicament. Resistor size, nozzle diameter, height of fluid column, and fluid barrier encroachment also may have an effect.

As indicated in connection with the third ejection chamber of FIG. 3, once a vapor droplet (e.g. 62) has been ejected, and the ejection element deactivated (e.g. cooled), medicament may again flow into the ejection chamber, effectively filling the ejection chamber with a new charge of medicament upon formation of a meniscus adjacent the ejection orifice.

The ejection element may take any of various forms, including for example, a resistor capable of independent activation by the inhaler's controller. When the resistor of a particular ejection chamber receives an electronic signal from the controller, the resistor may produce sufficient heat to eject a medicament vapor droplet from the corresponding ejection chamber. Such chamber activation typically occurs repetitively and in rapid succession. The rate of repetition and level of current applied are controllable. Ejection elements 42 may also take the form of piezoelectric transducers. Correspondingly, when the transducer receives an electronic signal from the controller, the transducer may produce enough voltage to eject medicament from within the ejection chamber. In either case, the presently described metered dose inhaler may produce an inhalant stream without the use of an aerosol carrier or propellant.

As indicated previously, and referring again to FIG. 1, the duration, intensity, and/or other characteristic of the electronic signal may be altered to effect changes in the medicament dosage and/or ejection characteristic. Processor 14 thus may be configured, for example, to determine whether and how electronic signal 24 is to be altered in response to sensed or calculated information relating to an indication of a characteristic of ejection fluid.

The metered dose ejector may be adapted to produce droplets within a consistent size range by controlling the effective size and shape of the vaporization chambers and ejection orifices, and the characteristics of the electronic signals and medicament in the ejection chambers. Because consistent droplet size can be produced as a function of the characteristics of the vaporization chambers, ejection orifices, electronic signals and ejection fluid, careful selection of the vaporization orifice characteristics and/or of the electronic signals allows the present ejector to reliably produce droplets having diameters within a desired range. The desired diameter may vary depending on the intended use, and the particular medication, but may be between 1 and 5 micrometers in an exemplary embodiment.

Ejection elements may be controlled independently, as discussed above, or may be controlled in groupings or subsets of a full set. By electronically controlling the rate of ejection element activation, it is possible to control the rate of medicament ejection, and thus the medicament dosage and drop sizes produced by the inhaler. This may be accomplished, whether the vaporization elements are controlled together, or in groupings or subsets. Similarly, dosage may be controlled by selectively activating various groupings or subsets of the ejection elements, or by some combination of operating parameters, including firing rate, pressure and quantity control.

Referring to FIG. 4, yet another embodiment of an inhaler according to the present invention is shown generally at 70. Inhaler 70 includes a housing 72 having a mouthpiece 74 that provides an exit port for the ejected inhalant. A storage chamber 76 stores medicament and provides it to ejection chambers as described above in an ejection mechanism 78. Operation of ejection mechanism is controlled by a controller 80 that receives power from a power supply 82. The power supply may be a battery, external power source, or other suitable power supply, whether disposable, rechargeable or permanent.

Operation of the inhaler may be initiated by an activation switch 84 controlled by the user, or the inhaler may instead detect the inhalation by the user, and activate the inhaler automatically. An output device, such as an alarm 86 may be used to notify the user of the operating condition of the inhaler, such as when medicament supplies are getting low or are too low, or when functioning of the inhaler is interrupted, as discussed below.

A sensor 88, shown attached to the storage chamber may detect an indication of a characteristic of the medicament in the ejection chambers. Sensor 88 may be placed in any position on the inhaler that will provide appropriate sensing. For instance, when placed on or in the storage chamber, as shown, it may be used to detect a corresponding condition, referred to generally as an indication, such as the temperature or pressure of fluid in the storage chamber, the volume of fluid in the storage chamber, the pressure or tension produced by a pressure-producing element, such as a spring, when the storage chamber is a compliant chamber, or even the orientation of the reservoir relative to gravity. The term indication is intended to refer to a sensed condition from which a characteristic of the medicament in the ejection chamber may be derived. For example, by sensing the backpressure or temperature of the fluid in the storage chamber or in an ejection chamber, the backpressure or temperature of the fluid in all of the ejection chambers may be derived.

Other positions and configurations may also be apparent. For instance, placing a temperature or pressure transducer in an ejection chamber, or employing a non-functioning sensing chamber, may be possible. Characteristic sensing in each ejection chamber may also be provided, even though such a configuration may be more complex and costly. Additionally, sensing the orientation of the housing may provide information about the orientation of the storage chamber, and thereby, information about backpressure in the ejection chambers can be derived. Such a characteristic may be any aspect of the medicament or the ejection chamber that affects the quality and quantity of the ejected medicament. For example, the backpressure of the medicament in the ejection chamber, or the temperature may determine drop size, and therefore the ultimate dosage and absorbability of the inhalant by the user.

As has been mentioned, in some ejection mechanisms, such as those that are of the form illustrated in FIGS. 2 and 3, functioning of the ejection mechanism may be dependent upon the condition of the fluid in the ejection chamber. An ejection chamber may be designed based on nominal or standard characteristics of the fluid in the ejection chamber. This may include the fluid vaporizing and flow characteristics as applied to a vaporization chamber design.

Characteristics of the ejection fluid that may affect operation may include the backpressure from the storage chamber and the temperature. Information about the backpressure may be derived from various sources, one or more of which may be detected as indications of the actual backpressure in the ejection chambers. Such sources include but are not limited to the relative pressure of fluid in the storage chamber, the actual pressure in the ejection chambers, the amount of fluid in the storage chamber, the number of doses that have been administered or that remain, the size or position of a spring-biased compliant storage chamber, or the orientation of the storage chamber relative to gravity. Similarly, the temperature of the stored or ejection fluid may be detected as actual indications of temperature of the fluid, or of the substrate forming the base for the ejection chamber, or may be calculated based on the rate and durations of activations of the ejection elements. These indications may thus be computed or counted by the controller, or may be determined by direct measurement or sensing of an associated condition in the inhaler.

Figure 5:
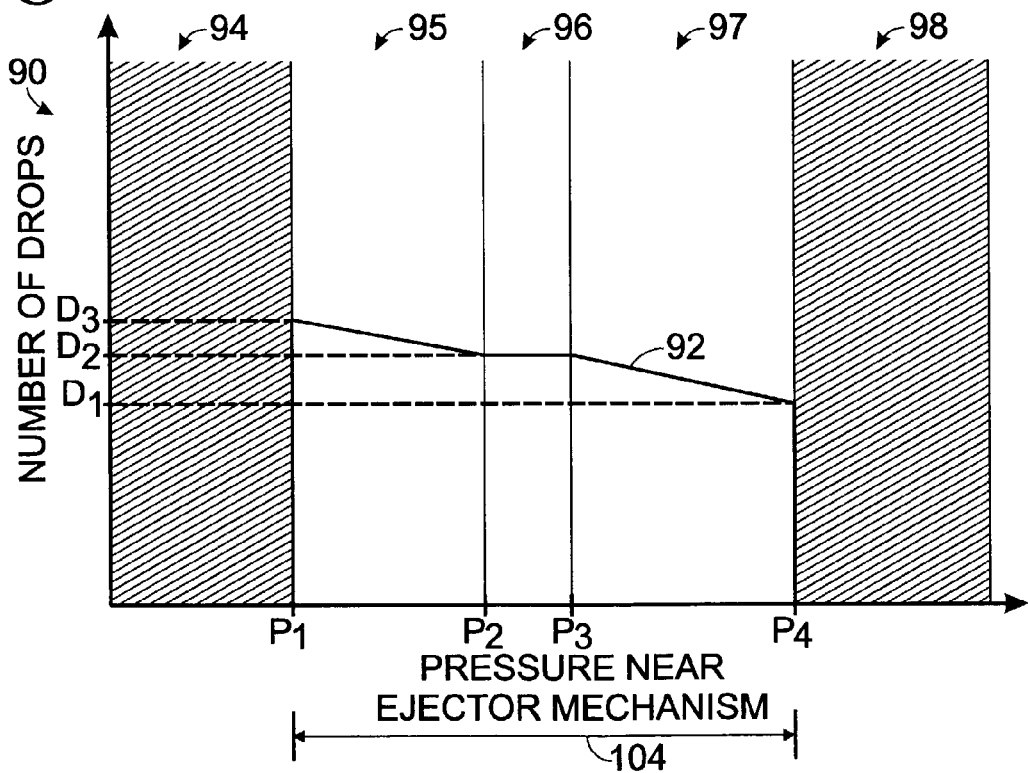
FIG. 5 is a chart illustrating exemplary operation of a medicament ejector according to an embodiment of the present invention.
Figure 6:
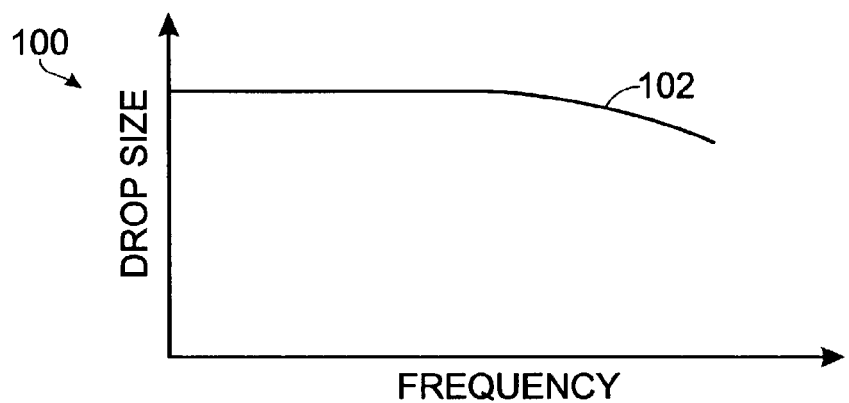
FIG. 6 is a chart illustrating an exemplary operating feature of a medicament ejector according to an embodiment of the present invention.

FIG. 5 illustrates an example of an operating regime that may be used for controlling operation of an ejector. A chart 90 is shown illustrating a line 92 of intended operation, in which in this example shows the number of drops ejected as a function of the pressure of the stored fluid near the ejector mechanism. For illustration purposes, five ranges of operating pressures are shown. More or fewer ranges could be used. Pressures $P_1$, $P_2$, $P_3$ and $P_4$ define the boundaries between the respective ranges 94, 95, 96, 97 and 98.

Figure 4:
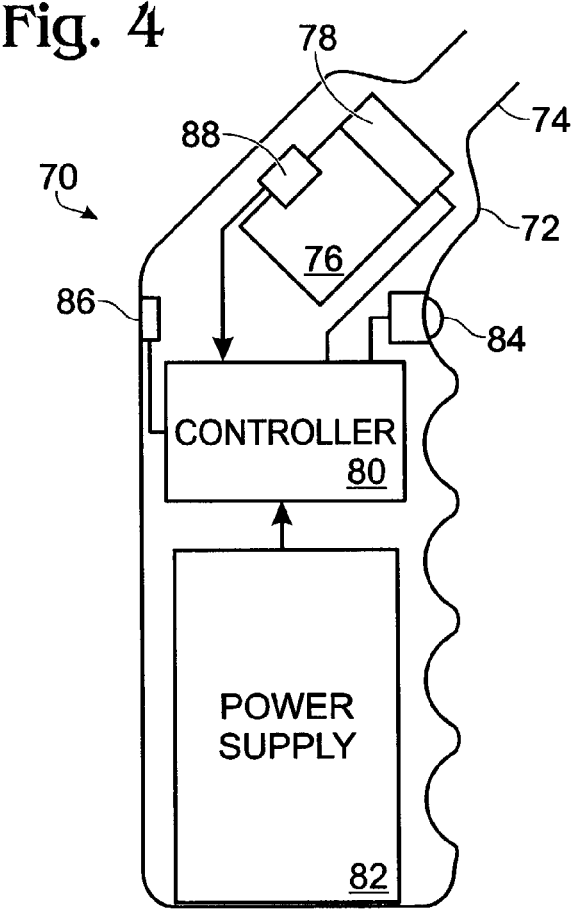
FIG. 4 is a block diagram of a medicament ejector according to yet another embodiment of the present invention.
Figure 7:
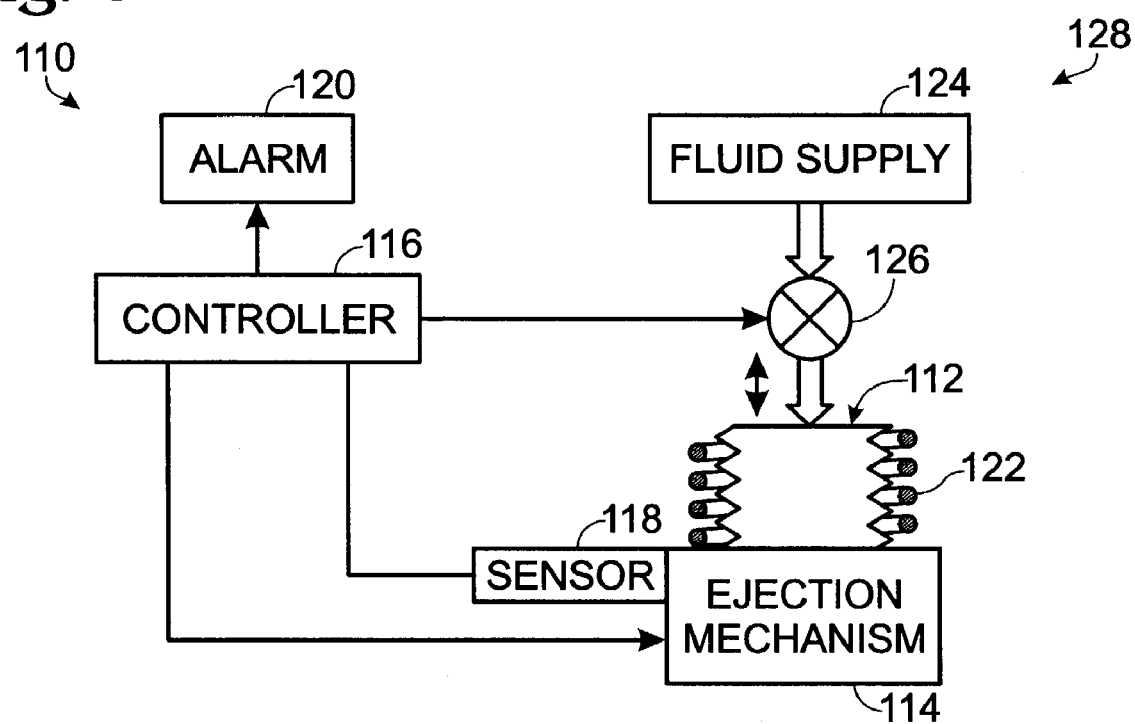
FIG. 7 is a block diagram of a medicament ejector according to yet another embodiment of the present invention.

Lowest range 94, including pressures below $P_1$, and highest range 98, including pressures above $P_4$, are ranges in which the pressures may be considered to be too low or too high to be able to make compensating adjustments in the operation of the ejection mechanism and still provide an ejected dosage of desired dosage and drop size. Operation of the inhaler thus may be blocked in these pressure ranges such that no drops are ejected.

Center range 96 between pressures $P_2$ and $P_3$ represents what may be considered a target range in which a somewhat consistent number of drops $D_2$ are ejected for detected or derived pressures between $P_2$ and $P_3$. Normal operating parameters may be used for pressures in this range. In a given embodiment, this range may be very narrow or even have zero width, as appropriate.

In lower and upper intermediate ranges 95 and 97, which respectively correspond to pressures within ranges $P_1$-to-$P_2$ and $P_3$-to-$P_4$, operating parameters may be modified or adjusted to compensate for a change in the pressure from a nominal or target pressure, or range of pressures.

When the pressure is low, as represented by range 95, the drop volume may be lower. In response to this, more drops may be ejected in order to deliver the same medicinal dosage. The number of drops thus may increase from the nominal number, $D_2$, to $D_3$ as the pressure drops from $P_2$ to $P_1$. This may be achieved by increasing the number of activations of the ejection elements. This action may have a two-fold effect: more drops may be ejected; and as the duration of firings increases, the substrate supporting the ejection chambers may increase in temperature, thereby increasing the drop size. This latter effect has a compounding impact that may be taken into consideration.

In addition, or alternatively, ejection elements in the form of resistors, or warming resistors in other types of systems, may be warmed directly by sending appropriate pulses of current or a continuous reduced current to them. These currents are insufficient to cause drop ejection. They may provide warming of the fluid by direct warming or warming of the associated substrate. In this way, the drop size that has been reduced by the lower pressure may be made larger, and therefore more normal, by increasing the temperature.

When the pressure is high, as represented by range 97, then the drop volume may be higher. In response to this, fewer drops may be ejected in order to deliver the same medicinal dosage. The number of drops thus may decrease from the nominal number, $D_2$, to $D_1$ as the pressure rises from $P_3$ to $P_4$. This may be achieved by decreasing the number of activations of the ejection elements.

Alternatively, the firing frequency actually may be increased. This alternative is appropriate for ejection chambers that are designed to refill incompletely between activations or firings of the ejection chambers when the firings occur at a fast enough rate. In other words, the duration between firings may determine the extent to which the ejection chambers refill with fluid. This configuration may be thought of as an overdamped drop generator architecture, as is shown by a graph 100 in FIG. 6. This graph shows, by a line 102, the drop size as a function of frequency of ejection element firing. As is shown, the drop volume or size may tend to be flat or constant for lower firing frequencies. However, as the firing frequency or rate increases, the drop size may progressively decrease. Thus, when backpressure is higher than normal, the firing frequency actually may be increased to reduce the drop size. For a given burst or series of activations, the overall volume or dosage may decline, compensating for the tendency of the drop size to increase with increasing pressure.

As a result of the foregoing, it will be appreciated that the controller also may be referred to as structure for maintaining constant, varying, and/or reducing to zero an operating parameter of an ejector.

As has been mentioned, the sizes of operating ranges 94, 95, 96, 97 and 98 may vary in width according to the characteristics of a given ejection mechanism and desired operating procedure. Thus, in a simple system, intermediate ranges 95 and 97 may not exist. A central or normal range 96 may exist only as a point, in which case $P_2$ would equal $P_3$. This latter case would be equivalent to having a single extended operating range 104 consisting of ranges 95 and 97, in which compensating action may be taken between pressures $P_1$ and $P_4$ to adjust the number of drops, or to take other action, such as has been described.

Although linear and continuous relationships have been shown between dependent and independent variables (number of drops and pressure, respectively), other relationships (such as discontinuous, geometric or logarithmic) may be used as appropriate. Other relationships may also be used as a basis for defining ejector operation. For instance, operating relationships may be defined by the number of drops ejected, the applied ejector element current, or the ejection element activation frequency as a function of pressure, supply chamber fluid volume, number of doses ejected, or ejector orientation.

As a further example, and as has been discussed, a warming current may be applied prior to the activation current in order to raise the temperature and reduce the viscosity of the medicament in the ejection chamber. This may tend to increase the size of ejected drops. Temperature sensors in one or more ejection chambers, or in the storage chamber adjacent to the ejection mechanism may be used to provide indications of the temperature of the fluid in the ejection chambers. When the temperature of the ejection fluid decreases, drop size may correspondingly decrease, reducing the dosage and the ability of the user to absorb the ejected medicament. A further operating relationship may accordingly be developed that adjusts the supply or ejection chamber fluid temperature as a function of a sensed temperature, thereby compensating or correcting for the change in temperature. Alternatively, the number of drops ejected could be changed as a function of temperature change.

As a further example, an ejector may also be configured to directly adjust the backpressure of fluid in an ejection chamber in response to the determination of an indication of a characteristic of ejection fluid. An embodiment of such an ejector is shown generally at 110 in FIG. 7. Similar to ejector 70 shown in FIG. 4, ejector 110 may have a fluid storage chamber 112 in fluid communication with an ejection mechanism 114. Ejection mechanism 114 may be controlled by a controller 116 that receives a signal from a sensor 118. Sensor 118 may be mounted to provide information indicating the backpressure of medicament fluid on the ejection mechanism. The user may be provided information, or a signal, via an alarm 120.

In this embodiment, storage chamber 112 may be a compliant fluid chamber, such as is provided by a flexible bag or envelope on which a force acts, such as by a device, such as a spring 122, tending to expand the chamber. The spring or other force-producing device, acting on the compliant chamber typically provides the desired backpressure on the stored fluid, and thereby on the ejection fluid in the ejection chamber. A suitable pressure range, such as, for example, −2 to −6 inches (approximately −50 to −150 millimeters) of water gauge pressure, may be maintained.

As fluid is ejected from the ejection chambers, fluid is drawn into the ejection chambers from storage chamber 112. This, in turn, causes the storage chamber to collapse, compressing the spring and decreasing (e.g., becoming more negative) the backpressure.

A further fluid supply 124 may be included that is selectively in fluid communication with storage chamber 112 via a valve 126. Supply 124, valve 126, sensor 118 and controller 116 may be collectively referred to as a regulation system, and in this instance, as a pressure regulation system 128. Controller 116 controls the operation of valve 126. When the sensed pressure reaches a given threshold, controller 116 may open the valve, allowing more fluid to flow from fluid supply 124. As storage chamber 112 refills with fluid, the spring tension relaxes, increasing the backpressure in the supply and ejection chambers.

Figure 8:
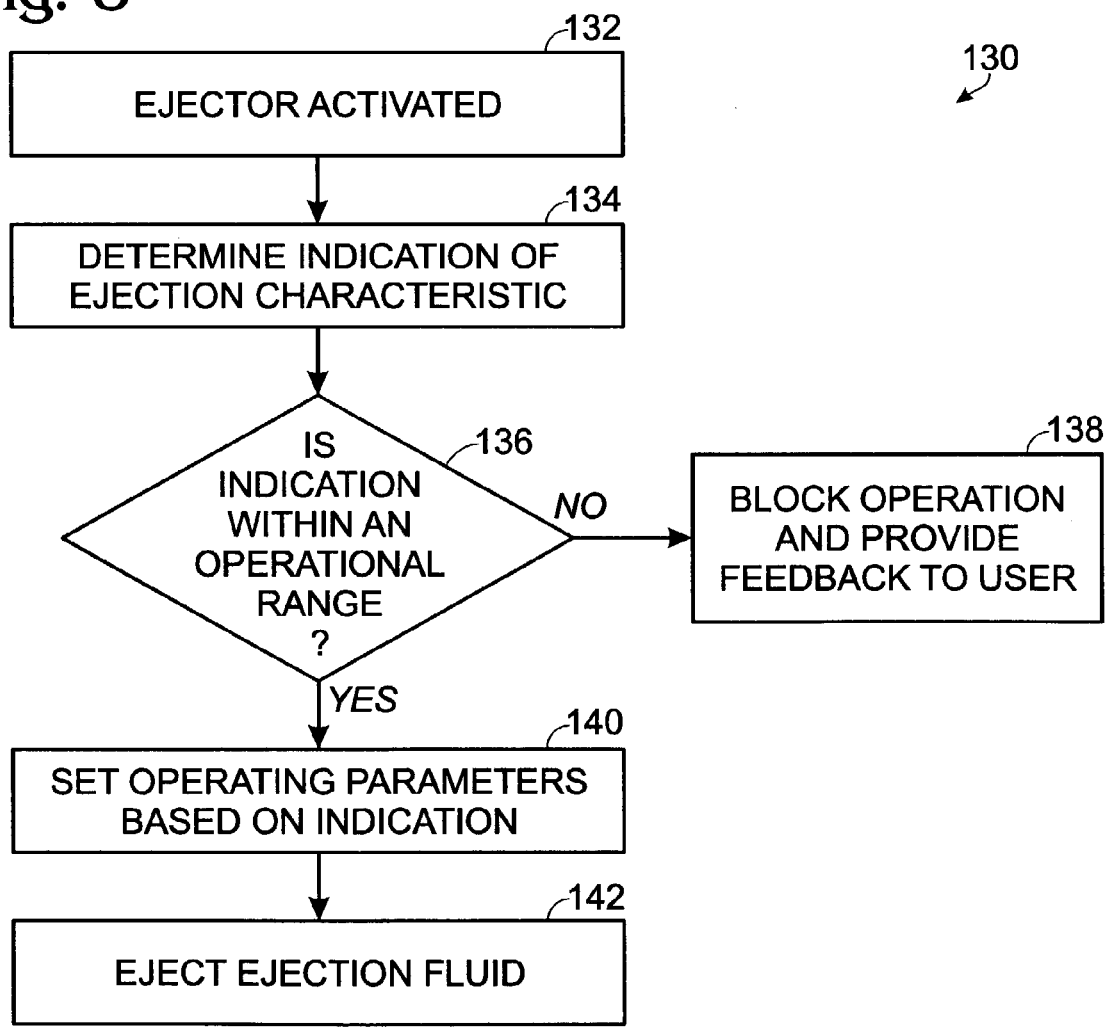
FIG. 8 is a flow chart demonstrating an exemplary method of ejecting a medicament in accordance with an embodiment of the present invention.

A general flow chart summarizing a method 130 for ejecting a medicament, such as may be used in administering an aerosol medicament to a user, is shown in FIG. 8. At 132, the ejector may be activated by input from a user or through automatic sensing of the user's action or presence by the device. Information that serves as an indication of a characteristic of the medicament in an ejection chamber may be determined at 134, such as provided by a sensor generating a signal relating to the backpressure.

A determination may be made at 136 as to whether the indication, or the ejection fluid characteristic derived from the indication, is within an operational range. Any of ranges 95, 96 or 97 shown in FIG. 5 may be considered an operational range. If not, operation may be blocked at 138 and the user notified, such as through an alarm. If the indication or ejection fluid characteristic is in an operational range, then appropriate operating parameters may be set at 140 based on the determined indication. If the indication is a pressure in normal range 96, then the normal operating parameters may already be set. If the indication is in a compensating range, such as either range 95 or 97, then operating parameters may be selected, as has been discussed, to compensate for any change in ejection fluid characteristics that may result from a determined change in one or more ejection fluid characteristics. The ejection mechanism may then be activated at 142 to eject ejection fluid having characteristics based on the determined indication.

While the present disclosure has been provided with reference to the foregoing preferred embodiments, those skilled in the art will understand that many variations may be made therein without departing from the spirit and scope defined in the following claims. The description should be understood to include all novel and non-obvious combinations of elements described herein, and claims may be presented in this or a later application to any novel and non-obvious combination of these elements. The foregoing embodiments are illustrative, and no single feature or element is essential to all possible combinations that may be claimed in this or a later application. Where the claims recite "a" or "a first" element or the equivalent thereof, such claims should be understood to include incorporation of one or more such elements, neither requiring nor excluding two or more such elements.

What is claimed is:

1. A medicament ejector comprising:

an ejection mechanism including at least one ejection chamber configured to contain a fluid-based solute medicament, and at least one ejection element, the ejection mechanism being configured to selectively effect controlled ejection of medicament from the at least one ejection chamber via activation of the at least one ejection element; a storage chamber configured to store the medicament, wherein the at least one ejection chamber is in continuous fluid communication with the storage chamber; and a controller configured to determine at least one indication of a characteristic of medicament in at least one of the ejection chamber and the storage chamber, and control ejection of medicament from the at least one ejection chamber based on the at least one determined indication, wherein the characteristic of the medicament is pressure of the medicament and wherein a current orientation of the ejection mechanism relative to a control orientation is determined from the at least one determined indication to control-ejection of medicament from the at least one ejection chamber based on the current orientation.

2. The medicament ejector of claim 1, wherein the controller is configured to determine whether the current orientation is within a given range of orientations relative to the control orientation.

3. The medicament ejector of claim 2, wherein the controller is configured to eject medicament from the at least one ejection chamber when the current orientation is within the given range of orientations and configured to not eject medicament from the at least one ejection chamber when the current orientation is outside the given range of orientations.

* * * * *